United States Patent [19]

Eisenberg

[11] Patent Number: 4,475,909
[45] Date of Patent: Oct. 9, 1984

[54] MALE URINARY DEVICE AND METHOD FOR APPLYING THE DEVICE

[76] Inventor: Melvin I. Eisenberg, 4080 Morrison Dr., Gurnee, Ill. 60031

[21] Appl. No.: 375,660

[22] Filed: May 6, 1982

[51] Int. Cl.$^3$ .............................................. A61F 5/44
[52] U.S. Cl. ................................. 604/349; 128/760
[58] Field of Search .................. 128/132 R, DIG. 15, 128/156, 157, 166, 760, 138 R, 149; 24/20 CW, 304, 67 AR, 20 W, 30.5 W; 156/213, 215; 604/327, 331, 346, 347, 349–352; 4/144.3

[56] References Cited

U.S. PATENT DOCUMENTS

| | | | |
|---|---|---|---|
| 2,303,131 | 11/1942 | Morgan | 128/156 |
| 4,187,851 | 2/1980 | Hauser | 604/352 |
| 4,237,584 | 12/1980 | Oetiker | 24/20 CW |
| 4,305,179 | 12/1981 | Sakurada | 24/20 CW |
| 4,378,018 | 3/1983 | Alexander | 128/760 |

FOREIGN PATENT DOCUMENTS

| | | | |
|---|---|---|---|
| 203038 | 2/1956 | Australia | 128/156 |
| 2096901 | 10/1982 | United Kingdom | 604/349 |

Primary Examiner—C. Fred Rosenbaum
Assistant Examiner—J. L. Kruter
Attorney, Agent, or Firm—Jerome Goldberg

[57] ABSTRACT

A male urinary device and method for applying for an incontinent patient comprising a sheath and a cushion strip interposed between the sheath and the penis. The cushion strip includes a seat portion and an arm extending out from one side of the seat and another arm extending out from the opposite side thereof. The second arm is positioned offset from the first arm so that the arms do not overlap on each other when wrapped around the penis. The seat and the arms are dimensioned so that the arms also do not overlap on the seat. The adjacent edges of the arms are applied to abut each other when the cushion strip encircles the penis and forms a continuous ring therearound, which is non-bulging on the upper surface thereof.

The cooperation of the sheath and the level cushion strip affords a liquid tight seal between the sheath and the cushion strip. The abutting adjacent edges of the arms prevent liquid leakage therebetween. Adhesive on the upper and lower surfaces of the cushion strip and on the inner edges of the arms of the strip further secures the liquid seal of the device. The sheath includes an outlet end for transmitting urine from the device to a receptacle tied to the patient's leg or waist.

24 Claims, 13 Drawing Figures

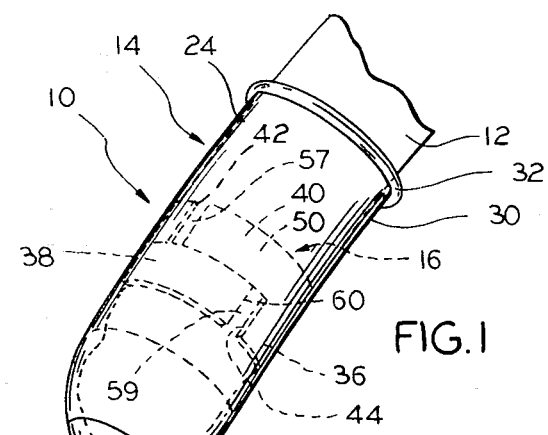
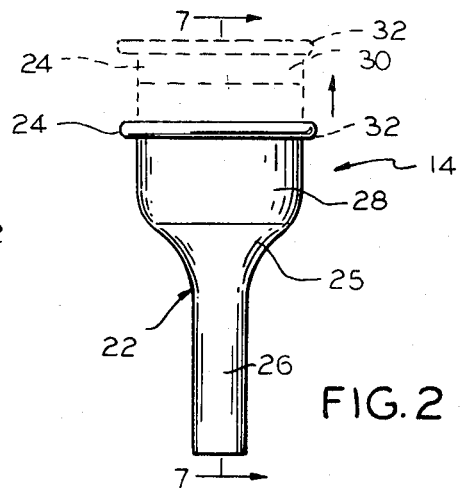
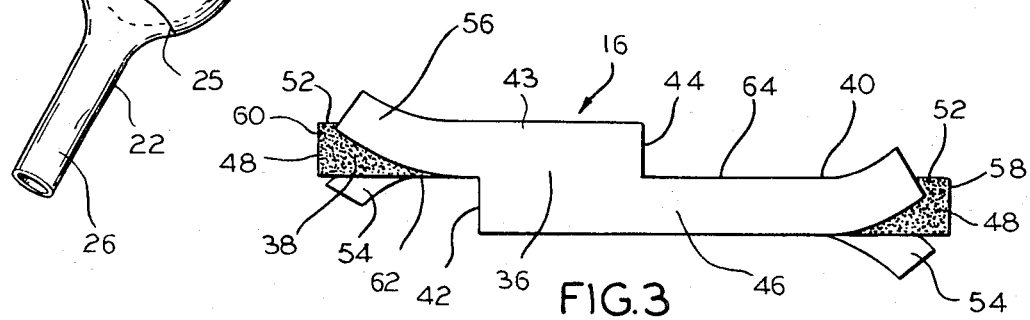
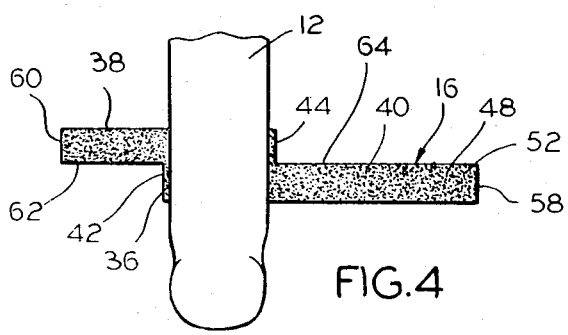
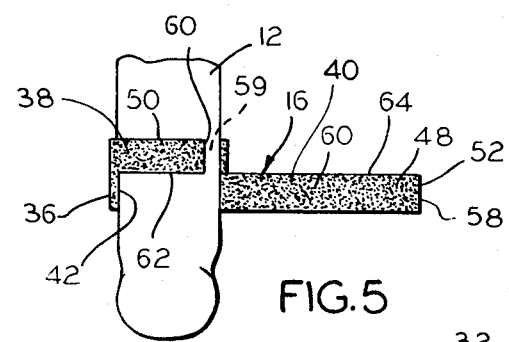
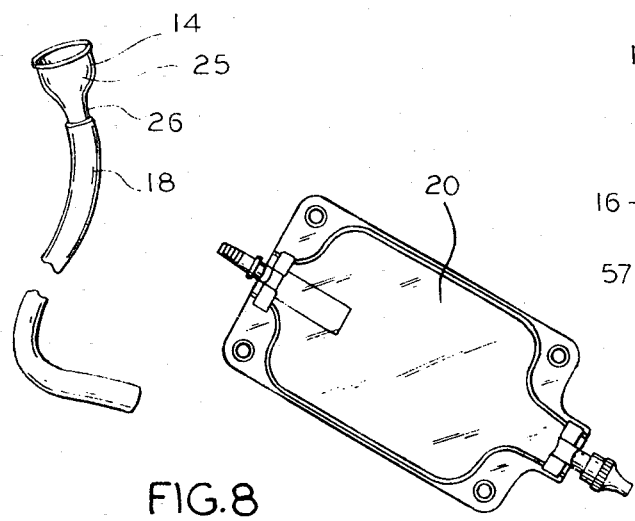
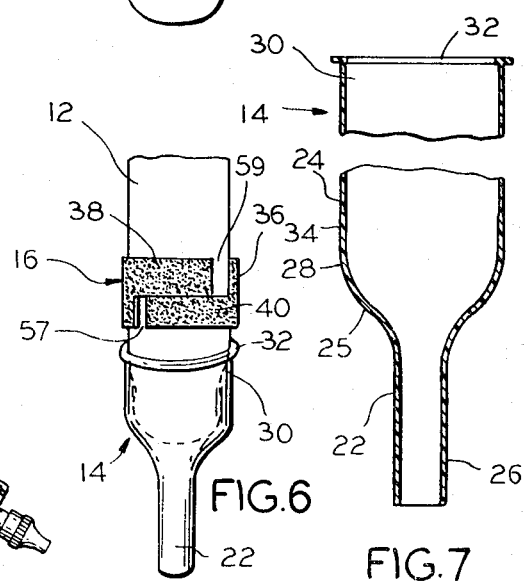

MALE URINARY DEVICE AND METHOD FOR APPLYING THE DEVICE

BACKGROUND OF THE INVENTION

This invention relates generally to an external catheter and more specifically relates to a male urinary device.

Male urinary devices have been proposed for and have been used by individuals or the incontinent patient having little or no control over his urinary functions.

Many prior male urinal devices included a flexible pouch to receive the penis and external securing means such as a length of tape or lace, to hold the pouch in place. Flexible tubing was usually used to connect the pouch with a substantially larger urine receptacle which was fastened around the waist or leg. These prior devices frequently constricted the penis and caused extreme discomfort. If the pouch were loosened to alleviate the problem, urine would seep out from the pouch and eventually the pouch would slip off.

More recent male urinary devices such as those disclosed in the Rogers et al U.S. Pat. No. 3,835,857, the Rogers et al U.S. Pat. No. 3,863,638, and the Hauser U.S. Pat. No. 4,187,851, comprised a thin pliable sheath of a plastic or rubber material, for extending over the penis and a resilient liner pad interposed between the sheath in an over lapping and spiral arrangement. The pad is adhesive on one or both sides thereof to prevent the sheath from slipping off the penis.

The last described urinary devices were generally less restrictive and more comfortable for the wearer than prior such devices. However, even these devices were susceptible to leakage due to the irregular and uneven bulges caused from the spiral and overlapping wrap of the liner pad. The subject invention overcomes this, by providing a cushion strip which is wrapped evenly around the penis without any overlapping.

SUMMARY OF THE INVENTION

The male urinary device of this invention comprises a sheath including a lower conical portion terminating into a tubular member and a thin membraneous body portion which unrolls to encase the penis. A cushion strip having a seat portion and at least two arms is interposed between the sheath body portion and the penis. One arm extends outward from one side of the seat and the second arm extends outward from the opposite side of the seat but in an offset position, so that the arms do not overlap when encircling or embracing the penis.

Moreover, the length of the seat and arms are dimensioned so that either arm does not overlap on the seat when the cushion strip is operatively wrapped on a normal flaccid penis.

The upper and the lower surfaces of the cushion strip may be coated with an adhesive substance, so that one surface adhers to the penis and the opposite surface to the sheath. Since the cushion strip does not overlap and, therefore, has substantially the same thickness or height around the entire circumference of the penis, the sheath firmly adhers to the adhesive on the cushion strip. This provides a liquid tight seal between the cushion strip and the sheath.

The edges of the strip may also be coated with an adhesive so that the adjacent edges of the embracing arms of the cushion strip firmly abut each other, to provide a continuous ring of the cushion strip around the penis, and thereby prevent fluid leakage between the arms. If the outer end of either encircling arms is spaced from the side of the seat, the adjacent contacting arm blocks fluid seepage via such space.

The cushion strip may comprise one arm extending out from one side of the seat and a second arm extending out from the opposite side of the seat but in an offset position, to prevent the overlapping of the arms when operatively wrapped around the penis.

The cushion strip may also comprise a pair of spaced apart arms extending out from one side of the seat, and a third arm extending out from the oposite side of the seat but offset from either of the other arms, to prevent the overlapping of the arms when operatively wrapped.

Accordingly, it is a primary object of the invention to provide a male urinary device for evacuating urine from the incontinent patient into a receptacle, which is securely and comfortably positioned on the penis in a liquid tight relationship.

Another object is to provide a male urinary device which does not leak urine out from the device.

Still another object is to provide a membraneous casing for covering a level and non-bulging upper surface of a cushion strip interposed between the casing and the penis in a liquid tight relationship, which is further sealed by adhesive on the cushion strip.

A primary feature of the invention is to provide a urinary device having a cushion strip interposed between a sheath and the penis which does not overlap, and extends around the penis in a continuous and level ring.

Another feature is to provide a urinary device including a cushion strip comprising a seat, an arm extending out from one side of the seat and a second arm extending out from the opposite side of the seat, and the adjacent edges of the arms firmly contact together, to form a continuous ring when the cushion strip is operatively wrapped around the penis.

Still another feature is to provide a urinary device comprising a cushion strip having a pair of spaced apart arms extending out from one side of the seat and a third arm extending out from the opposite side of the seat, and the arms being positioned and dimensioned not to overlap on to the seat or on to each other when operatively wrapped.

BRIEF DESCRIPTION OF THE DRAWING

Referring to the drawing in which the same characters of reference are employed to indicate corresponding similar parts throughout the several figures of the drawing:

FIG. 1 is a perspective view of a male urinary device embodying the principles of the invention, illustrating a sheath operatively positioned over the penis and showing in phantom a cushion strip interposed between the sheath and the penis;

FIG. 2 is a perspective view of the sheath in a non-operative rolled configuration and showing in phantom the sheath partially unrolled;

FIG. 3 illustrates the cushion strip and showing the upper and lower protective layers partially pulled off to view the adhesive surfaces;

FIG. 4 illustrates the penis resting on the seat of the cushion strip prior to wrapping the arms of the strip therearound;

FIG. 5 illustrates one arm of the cushion strip encircling the penis;

FIG. 6 illustrates both arms of the cushion strip embracing the penis and showing the sheath in position prior to being unrolled for encasing the cushion strip and the penis;

FIG. 7 is a cross sectional view of the sheath taken on the plane of the line 7—7 in FIG. 2 and viewed in the direction indicated; and FIG. 8 illustrates the urine evacuation system including the sheath, the receptacle bag and the flexible tubing for coupling the outlet of the sheath to the bag.

DESCRIPTION OF THE PREFERRED EMBODIMENT

Figure 9:
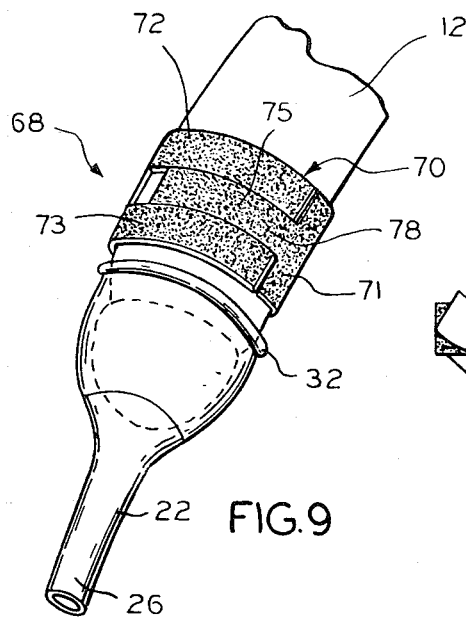
FIG. 9 is a perspective view of another embodiment of a male urinary device embodying the principles of the invention, having a cushion strip operatively positioned over the penis prior to inserting a sheath thereover.
Figure 10:
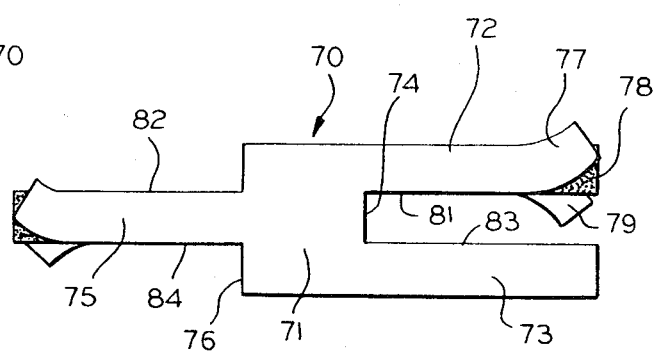
FIG. 10 illustrates the cushion strip of FIG. 9.

Referring to FIG. 1 of the drawing, a male urinary device indicated generally by the reference numeral 10 is shown operatively positioned on the penis 12 of the patient or user. The device 10 includes a sheath 14 (FIG. 2) and a cushion strip 16 (FIG. 3) interposed between the sheath 14 and the penis 12. A tubular connecting means 18 couples the urinary device 10 to a urine receptacle bag 20 (FIG. 8).

The sheath 14 comprises an outlet section 22 and a membraneous rollable casing 24. The outlet section 22 includes a cone part 25 terminating into a hollow tube member 26. An annular part 28 is formed between the cone part 25 and the casing 24. As may be seen from FIG. 7, the annular part 28 is constructed thinner than the cone part 25.

The upper part 30 of the casing 24 includes a flexible and sturdy band 32 (FIGS. 1, 2 and 7) on which the rolled layers of the casing 24 are supported. The band 32 enables the casing 20 to be easily unrolled for positioning on the penis, and also affords a firm core on which the casing 24 may be rewound when removing the casing 20 from the penis 12 to be reused.

The lower end 34 of the casing 24 is constructed slightly thicker than the remaining portion of the casing 24 between such lower end 34 and the band 32. This reinforces the casing 24 to prevent tearing and ripping, as it is unrolled and snugly pulled over the penis, and also enables greater and more frequent use of the same device 10.

The cushion strip 16 includes a seat portion 36 and a pair of arms 38,40. Arm 38 extends out from side 42 of the seat 36 at the upper part 43 of the seat, as viewed in FIG. 3. Arm 40 extends out from the opposite side of seat 36 at the lower part 46 of the seat, as also viewed in FIG. 3. Therefore, one arm is offset from the other to form substantially a "Z" configuration.

An adhesive substance 48 is coated over the top surface 50 (FIGS. 5 and 6) of the cushion strip 16 and also over the bottom surface 52 (FIGS. 3, 4 and 5) thereof. A protective layer 54 adhers to the adhesive 48 on the top surface 50, and similarly a protective layer 56 adhers to the adhesive on the bottom surface 52. The layers 54,56 are easily pulled off from the strip 16.

The seat 36 and the arms 38 and 40 of the cushion strip 16 are dimensioned so that when the arms embrace the penis, they do not overlap on the seat 36 and do not create any gaps through the width of the cushion strip 16, as will be more fully described below. Arm 38 is shown in the various figures of the drawing shorter in length than arm 40. The arms 38,40 may be of the same length, one arm shorter than the other or both arms short, provided that, as aforesaid, the arms do not overlap on the seat, or cause a gap or gaps through the width of the cushion strip 16. Therefore, the wrap of the cushion strip forms a single continuous turn or ring around the penis which is non-bulging and the outer surface of the cushion strip is substantially even or level.

Turning now more particularly to FIGS. 1 and 6, it will be seen that a space 57 separates the outer end 58 of the longer arm 40 from the side 42 of the seat 36, and a larger space 59 separates the outer end 60 of the shorter arm 38 from the side 44 of the seat 36. Specifically note that the spaces 57 and 59 are not in alignment with each other, and thus, do not cause gaps through the wrapped cushion strip 16.

Any urine seepage that may back up via space 57 is blocked by arm 38 if the cushion strip is wrapped in the manner shown in FIG. 6. Also, any urine seepage that may back up via space 59 is blocked by arm 40 if the cushion strip 16 is wrapped in the reverse manner, as shown in FIG. 1.

If the urinary device 10 is used for a child or patient having a smaller than normal adult penis, a piece from the outer end 58 of the longer arm 40 should be cut off, so that the wrap of the arms 38,40 will encompass not more than a single continuous turn, and, hence, would not overlap on to the seat 36. Therefore, the reduction of the length of the cushion strip 16 will provide the level and non-bulging configuration even for the smaller than normal penis.

The inner edges 62,64 of the arms 38,40 also have the adhesive substance 48 thereon. When wrapping the arms 38,40 the inner edges 62 of arm 38 and inner edge 64 of arm 40 are brought into contact with each other and firmly secure together due to the adhesive 48, thereby providing a barrier against liquid leakage therebetween. The adhesive 48 affords firm contact but permits easy release of one surface from the contacting surface.

With particular reference to FIGS. 4, 5 and 6, the placing of the device 10 on the patient will be described. The protective layers 54 and 56 are removed from the cushion strip 16. The penis is initially positioned on the seat 36 of the cushion strip 16 (FIG. 4). Arm 38 is wrapped around the penis in one direction and the outer end 60 is spaced from side 44 of seat 36 (FIG. 5). Arm 40 is then wrapped around the penis in the opposite direction and the outer end 58 is slightly spaced from side 42 of seat 36 (FIG. 6). The inner edges 62,64 of the arms 38,40 should abut each other but not in any way overlap each other. Slight inward pressure should be applied to the arms 38,40 so that the adhesive on the inner edges 62,64 cause the inner edges 62,64 to firmly adhere to each other. Pressure should also be applied to the top of the cushion strip 16, so that the adhesive 48 adhers to the penis.

The head of the penis is now inserted into the outlet section 22 of the sheath 14 (FIG. 6). The casing 24 is unrolled off the band 32 upward to the cushion strip 16.

The band 32 may be stretched outward slightly, to permit passing over the cushion strip 16 without making any appreciable contact with the adhesive 48. The casing 24 is held taut after the band 32 has moved past the cushion strip 16 to provide a skin tight association of the sheath 14 with the cushion strip 16. The unrolling of the casing 24 is continued along the penis until reaching a substantial distance above the cushion strip, as seen in FIG. 1. The casing 24 need not be completely unrolled at this point or level. Slight pressure is applied to that portion of the casing 24 in contact with the strip 16 to insure firm adherence of the sheath 14 with the adhesive 48 of the cushion strip.

Now the tubular connecting means 18 is connected to the outlet tube member 26 of the male urinary device 10 on one end, and connected to the urine receptacle bag 20 (FIG. 8) on the other end. The receptacle bag 20 is tied to the user's leg or waist.

The thin membraneous casing 24 of the sheath 14 affords a skin tight association with the penis and also with the cushion strip 16. Since the cushion strip 16 does not bulge and is level when operatively encircling the penis, the sheath is in continuous and non-interrupted contact with the top of the cushion strip and thereby prevents leakage of urine between the sheath and the cushion strip. Similarly, the continuous and uninterrupted contact of the bottom of the cushion strip 16 with the penis, held in place by the taut sheath slightly compressing the cushion strip, also prevents urine leakage between the cushion strip and the penis. The effect of the snug association of the sheath with the cushion strip also maintains positive contact between the inner edges 62,64 of the arms 38,40. The adhesive 48 further assures the maintainance of the liquid tight relationship between the sheath and the cushion strip.

As above indicated, the top and bottom of the cushion strip 16 may be used interchangeably. FIGS. 4, 5 and 6 illustrate the use of the strip 16 one way, and FIG. 1 shows the strip used in the opposite manner.

The cushion strip 16 is constructed from material which is flexible, readily compressible, resilient and water resistant. A plastic such as a polyvinyle chloride or a combination of rubber and polyvinyle chloride may be used.

The adhesive substance 48 applied to the cushion strip 16 may be any suitable pressure sensitive adhesive which would not cause irritation or have any allergic effect upon contact with the user's skin.

The sheath may be a suitable plastic or rubber(latex) which covers the penis tautly and snugly, without causing discomfort or irritation. It should further have sufficient resiliency and strength, so that the membraneous casing may be rolled and unrolled as desired, for removing and reapplying the urinary device to the patient. The sheath must also be water resistant.

Turning now specifically to FIG. 9, another embodiment of a male urinary device is illustrated and identified generally by the reference numeral 68. The device 68 comprisises a cushion strip 70 which is flexible and compressible, and similarly constructed as the cushion strip 16. The strip 70 comprises a seat protion 71, a pair of spaced apart outside arms 72,73 extending outward from the side edge 74 of the seat 71 and an inside arm 75 extending outeard from the opposite edge 76 of the seat. A protective layer 77 adhers to the top surface 78 of the strip 70, and another protective layer 79 adheres to the bottom surface 80 of the strip 70. The layers 77,79 are similarly constructed as the layers 54,56 of the strip 16 (FIG. 3) and are easily pulled off from the strip 70. The adhesive substance 48 is coated over the top and bottom surfaces 78,80.

The seat 71 and the arms 72,73 and 75 of the strip 70 are dimensioned so that when the arms embrace the penis, they do not overlap the seat 71 and do not create any gaps through the width of the cushion strip 70. Thus, the wrap of the cushion strip 70 forms a single continuous turn or ring around the penis which is non-bulging and the outer surface of the cushion strip is substantially even or level.

When wrapping the arms 72,73 and 75 around the penis, edge 81 of arm 72 should be in contact with edge 82 of the inside arm 75, and the inner edge 83 of arm 73 should be in contact with the opposite edge 84 of arm 75, A space 85 separates the outer tip 86 of arm 75 from side edge 74 of the seat 71. The outer tip 87 of arm 72 and the outer tip 88 of arm 73 should be in contact with the edge of side 76 of the seat 71, but may be spaced from side 76 if the arms 72,73 do not reach.

The arms 72,73 provide a barrier against urine seeping out from the device 68 via the space 85. The inside arm 75 may be brought into contact with the side 74 of the seat 71(but should not overlap on to the seat 71), provided that the increased tension would not cause pain or contriction of the penis. The arms 72,73, as aforesaid, may be spaced from the side 76, and the inside arm 75 would block and prevent any urine leakage.

Figure 11:
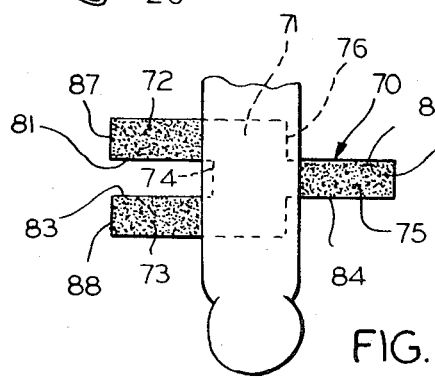
FIG. 11 illustrates the penis resting on the seat of the cushion strip of FIG. 10 prior to wrapping the arms of the strip therearound.
Figure 12:
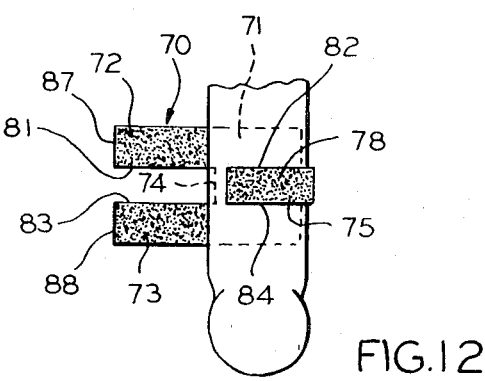
FIG. 12 illustrates the inner arm of the cushion strip of FIG. 10 encircling the penis.
Figure 13:
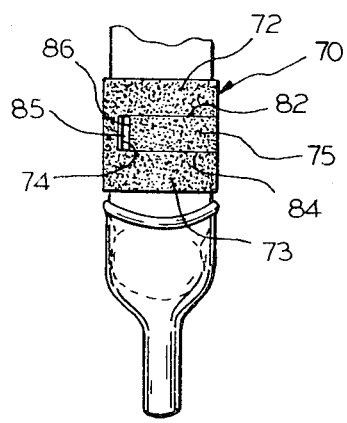
FIG. 13 illustrates all the arms of the cushion strip of FIG. 10 encircling the penis.

Referring now to FIGS. 11, 12 and 13, the wrapping cushion strip 70 will be described with more particularity. The protective layers 77 and 79 are removed from the cushion strip 70. The penis is initially positioned on the seat 71 of the cushion strip 70 (FIG. 11). The inside arm 75 is wrapped around the penis in one direction toward side 74 of the seat 71. The embrace should be firm, but should not constrict or pain the penis. The outer tip 86 may be brought into contact with side 74 of the seat 71, but should not overlap on to the seat 71. The outer tip 86 may be spaced from the side 74 (FIG. 13), if contact with side 74 would be too tight a wrap.

The outside arms 72 and 73 are now wrapped around the penis in the opposite direction, so that the inner edge 81 of arm 72 is placed in contact with edge 82 of the inside arm 75, and the inner edge 83 of arm 73 is placed in contact with edge 84 of the inside arm 75, but neither arm 72 or 73 should overlap on to arm 75. The outer tips 87 and 88 should be brought into contact with side 76 of seat 71 but should not overlap thereon. The arms 72, 73 are slightly longer than the inside arm 75, so that contact with side 76 of seat 71 could be made without constraining the average adult sized penis. However, if the length of the arms 72,73 are too long, a piece from each tip could be cut off so that the desired wrap could be achieved. On the other hand, if the arms 72,73 are too short to reach contact with side 76 of seat 71, the outer tips 87, 88 should be comfortably positioned spaced from the side 76.

The adhesive substance 48 insures a firm contact of the arm edges with each other and a firm contact of the outer tips of the arms with edges of the sides 74, 76 of the seat 71, if they reach to make contact therewith.

Slight inward pressure should be applied to the cushion strip, so that adhesive 48 on the edges 81,83 of the outside arms 72,73 firmly adheres to the adhesive 48 on the opposed edges 82,84 of the inside arm 75. Pressure should also be applied to the top of the cushion strip 70, so that the adhesive adhers to the penis. Now the penis with the cushion strip 70 securely but comfortably positioned thereon is inserted into the sheath 14, as described above.

Various modifications of the invention of a male urinary device and method for applying same described herein are within the spirit and scope of the invention, the scope of which is limited soley and defined by the appended claims.

I claim:
1. A male urinary device comprising:
   a sheath for positioning over the penis and including an outlet end for evacuating urine;
   a cushioning means for interposing between the sheath and the penis and including a seat and at least two arms, one of said arms extending outward from one side of the seat and the second of said arms extending outward from the opposite side of the seat, said one arm being wrapped around the penis in one direction and said second arm being wrapped around the penis in the opposite direction, said cushioning means being wrapped around the circumference of the penis without either of said arms overlapping said seat or the other of said arms; and
   each of said arms including an inner edge, the inner edges of said arms being opposed and in contact with each other when said arms are wrapped.
2. The device of claim 1, wherein said seat includes an upper portion and a lower portion and said one arm extends out from a part of said one side adjacent said upper portion and said second arm extends out from a part of said opposite side adjacent said lower portion to form substantially a "Z" configuration, said arms being adjacent to each other when wrapped around the penis.
3. The device of claim 1, wherein the length of each of said arms and said seat are dimensioned so that the outer end of each of the arms lie on the penis and not on the seat.
4. The device of claim 1, wherein:
   a first space separates the outer end of said one arm from the opposite side of the seat when wrapped in said one direction; and
   a second space separates the outer end of said second arm from said one side of the seat when wrapped in said opposite direction, said first and second spaces not being in communication with each other since said second arm blocks said first space and said one arm blocks said second space.
5. The device of claim 1, wherein said sheath includes:
   an outlet portion for evacuating urine from the device; and
   a membraneous covering formed to said outlet portion and snugly covering the cushioning means, said cushioning means being substantially non-bulging and level inside said covering throughout the circumference of the cushioning means.
6. The device of claim 1, wherein said cushioning means is a continuous ring and includes no opening passing through the width thereof when the cushion strip is operatively wrapped around the penis.
7. The male urinary device of claim 1, wherein said cushioning means includes:
   a third arm spaced from said one arm and extending outward from said one side of the seat, said third arm being wrapped around the penis in said one direction, said second arm being positioned in the space between the first and third arms, the inner edge of said third arm being opposed to and in contact with the outer edge of the second arm when the arms are wrapped, said third arm being wrapped on said penis without overlapping said seat or the other said arms.
8. The device of claim 7, wherein said seat includes:
   an upper part, a lower part, and an intermediate part between said upper and lower parts, one of said pair of arms extending outward from said one side at said upper part and the other of said pair of arms extending outward from said one side at said lower part, said third arm extending outward from said opposite side of said seat at said intermediate part, whereby said arms and seat form a substantially "Y" shaped configuration.
9. The device of claim 7, wherein:
   one of said pair of arms includes an inner edge contacting the edge on one side of the third arm, and the other of said pair of arms includes an inner edge contacting the edge on the opposite side of the third arm, when said cushioning means is operatively wrapped around the penis.
10. A male urinary device comprising:
    a sheath for positioning over the penis and including an outlet end for evacuating urine;
    a cushioning means for interposing between the sheath and the penis and including:
    a seat;
    a pair of spaced apart arms extending from said one side of the seat to wrap around the penis in said one direction; and
    a third arm extending outward from said opposite side of the seat to wrap around the penis in said opposite direction and between said other arm, said cushioning means being wrapped around the circumference of the penis without any of said arms overlapping said seat or the other of said arms;
    one of said pair of arms including an inner edge for contacting the edge on one side of the third arm, and the other of said pair of arms including an inner edge for contacting the edge on the opposite side of the third arm, when said cushioning means is operatively wrapped around the penis; and
    a coating of adhesive disposed on each of said edges for securing the edges, said edges being easily detachable when unwrapping the cushioning means.
11. The device of claim 1, wherein:
    a space separates the outer end of one of said arms from the opposite side of the seat when said cushioning means is wrapped around the penis.
12. A male urinary device comprising:
    a sheath for positioning over the penis and including an outlet end for evacuating urine;
    a cushioning means for interposing between the sheath and the penis and including a seat and at least two arms, one of said arms extending outward from one side of the seat and the second of said arms extending outward from the opposite side of the seat, said one arm being wrapped around the penis in one direction and said second arm being wrapped around the penis in the opposite direction, said cushioning means being wrapped around the circumference of the penis without either of said arms overlapping said seat or the other of said arms;
    each of said arms including an inner edge, the inner edges of said arms being opposed and in contact with each other when said arms are wrapped; and the inner edges of said arms including adhesive means for securing said edges together.

13. A male urinary device comprising:
a sheath for positioning over the penis and including an outlet end for evacuating urine;
a cushioning means for interposing between the sheath and the penis and including a seat and at least two arms, one of said arms extending outward from one side of the seat to wrap around the penis in one direction and the other of said arms extending outward from the opposite side of the seat to wrap around the penis in the opposite direction, said arms and seat being dimensioned so that the arms do not overlap on the seat or the other of said arms when wrapped around the penis;
a first space separates the outer end of said one arm from the opposite side of the seat when wrapped in said one direction;
a second space separates the outer end of said other arm from said one side of the seat when wrapped in said opposite direction, said first and second spaces not being in communication with each other since said opposite arm blocks said first space and said one arm blocks said second space;
each of said arms including an inner edge, the inner edges of said arms being opposed and in contact with each other when said arms are wrapped; and
said inner edges having adhesive for securing said edges together.

14. A method for applying a male urinary device to a flaccid penis including the steps of:
providing a cushion strip including a seat, one arm extending out from one side of the seat and another arm extending out from the opposite side of the seat;
positioning the penis on the seat of the cushion strip;
wrapping one arm of the strip around the penis in one direction toward the opposite side of the seat but not to overlap the seat;
wrapping the second arm of the strip around the penis in the opposite direction toward said one side of the seat but not to overlap the seat or said one arm;
contacting the inner edge of said one arm with the inner edge of the other arm;
providing a sheath having an outlet end for evacuating urine;
inserting the head of the penis in said outlet end; and
covering said penis and said wrapped cushion strip with said sheath.

15. The method of claim 14, wherein said sheath includes a casing formed of a thin material and a band at the outer end of the casing and said casing being rolled on said band when said sheath is in a non-operative position, and said method further including:
unrolling the casing from the band for covering the penis and the wrapped cushion strip.

16. The method of claim 15 further includes:
rolling said band downward past the wrapped cushion strip and toward the head of the penis for removing the sheath from the penis and thereby storing successive layers of said casing on said band.

17. The method of claim 16, wherein both sides of said cushion strip have adhesive thereon, said method further includes:
applying pressure on said portion of the casing contacting said cushion strip after said casing is positioned on the penis to cause firm adherence of the casing with the wrapped cushion strip.

18. The method of claim 14 wherein one of said arms is longer than the other arm, and said method includes:
cutting off a predetermined length from said longer arm prior to wrapping said longer arm around the penis to prevent overlapping of said longer arm on said seat.

19. The method of claim 14 includes:
cutting a predetermined length from one of said arms prior to wrapping said one arm to prevent said one arm from overlapping on said seat.

20. The method of claim 14 includes:
spacing the outer end of said one arm from said opposite side of the seat; and
spacing the outer end of the other arm from said one side of the seat, said contacting of said inner edges blocking any opening through the width of said wrapped cushion strip.

21. A method for applying a male urinary device on to a penis including the steps of:
providing a cushion strip including a first arm and a second arm spaced apart from each other and extending out from one side of the seat and a third arm extending out from the opposite side of the seat, said first and second arms including inner edges normally opposed to each other;
positioning the penis on to the seat;
wrapping said third arm on the penis toward said one side of the seat but not to overlap on to the seat;
wrapping said first arm on the penis toward said opposite side of the seat but not to overlap on to the seat;
contacting the inner edge of said one arm with the adjacent edge of said wrapped third arm;
wrapping said second arm on the penis toward said opposite side of the seat but not to overlap on to the seat;
contacting the inner edge of said second arm with the adjacent edge of said wrapped third arm which is opposite to the edge in contact with said first arm;
inserting the penis with the cushion strip wrapped thereon into a sheath; and
covering said wrapped cushion strip with said sheath.

22. The method of claim 21, wherein said third arm is wrapped on said penis between said first and second arms.

23. The method of claim 22, wherein adhesive is applied on the edges of said arms and said method further includes:
applying lateral pressure to said arms so that said edges firmly adhere to each other.

24. The method of claim 22, wherein adhesive is applied on said cushion strip and said method still further includes:
applying downward pressure on said strip so that the strip adhers to the penis and lateral pressure to said arms so that said edges firmly adhere to each other.

* * * * *